(12) United States Patent
Ishikawa et al.

(10) Patent No.: US 6,338,034 B2
(45) Date of Patent: Jan. 8, 2002

(54) METHOD, APPARATUS, AND COMPUTER PROGRAM PRODUCT FOR GENERATING A SUMMARY OF A DOCUMENT BASED ON COMMON EXPRESSIONS APPEARING IN THE DOCUMENT

(75) Inventors: Kai Ishikawa; Akitoshi Okumura, both of Tokyo (JP)

(73) Assignee: NEC Corporation, Tokyo (JP)

(*) Notice: Subject to any disclaimer, the term of this patent is extended or adjusted under 35 U.S.C. 154(b) by 0 days.

(21) Appl. No.: 09/061,096

(22) Filed: Apr. 16, 1998

(30) Foreign Application Priority Data

Apr. 17, 1997 (JP) .............................................. 9-100432

(51) Int. Cl.[7] .............................................. G06F 17/27
(52) U.S. Cl. .......................................... 704/9; 707/530
(58) Field of Search .................. 704/1, 9, 10; 707/530, 707/531, 532, 3, 4, 102

(56) References Cited

U.S. PATENT DOCUMENTS

| | | | | |
|---|---|---|---|---|
| 4,965,763 A | * | 10/1990 | Zamora | 704/9 |
| 5,077,668 A | * | 12/1991 | Doi | 704/9 |
| 5,297,027 A | * | 3/1994 | Morimoto et al. | 704/9 |
| 5,638,543 A | * | 6/1997 | Pedersen et al. | 704/9 |
| 5,689,716 A | * | 11/1997 | Chen | 704/9 |
| 5,778,397 A | * | 7/1998 | Kupiec et al. | 707/500 |
| 5,838,323 A | * | 11/1998 | Rose et al. | 345/349 |
| 5,848,191 A | * | 12/1998 | Chen | 382/229 |
| 5,857,184 A | * | 1/1999 | Lynch | 707/4 |
| 5,873,087 A | * | 2/1999 | Brosda et al. | 707/100 |
| 5,918,240 A | * | 7/1999 | Kupiec et al. | 707/531 |
| 5,924,108 A | * | 7/1999 | Fein et al. | 707/531 |
| 5,963,965 A | * | 10/1999 | Vogel | 707/501 |

FOREIGN PATENT DOCUMENTS

| | | | | |
|---|---|---|---|---|
| JP | 1-290076 | 11/1989 | ............ | G06F/15/38 |
| JP | 2-93866 | 4/1990 | ......... | G06F/15/401 |
| JP | 2-112069 | 4/1990 | ......... | G06F/15/401 |
| JP | 3-191475 | 8/1991 | ......... | G06F/15/401 |
| JP | 4-74259 | 3/1992 | ............ | G06F/15/20 |
| JP | 4-90055 | 3/1992 | ............ | G06F/15/38 |
| JP | 5-233729 | 9/1993 | ......... | G06F/15/401 |
| JP | 6-215049 | 8/1994 | ............ | G06F/15/20 |
| JP | 6-259423 | 9/1994 | ............ | G06F/15/20 |
| JP | 7-175808 | 7/1995 | ............ | G06F/17/27 |

OTHER PUBLICATIONS

Joachim, Jae–Hak et al., "Another Investigation of Automatic Text Summarization: A Reader Oriented Approach", Intelligent Information Systems 1994, Proceeding of the 1994 Second Australian and New Zealand Conference, 1994, pp. 472–476.*

Doi Nishimura "Japanese Language Text Summary" NEC Technical Report, vol. 47 No. 8, 1994, pp. 48–52 (Sep. 16, 1994).

Ando, Doi, Muraki "Information Extraction from Newspaper Articles and Providing a Multi–Language Index", Information Processing Society of Japan 48th (first half of 1994) National Conference Proceedings (3), p. 105–106 (Mar. 23, 1994).

* cited by examiner

Primary Examiner—Patrick N. Edouard
(74) Attorney, Agent, or Firm—Foley & Lardner (57) ABSTRACT

A method of summarizing a document which comprises the steps of: extracting sentence-constituting-elements from the document; tabularizing the sentence-constituting-elements corresponding to categories and sentences in the document; extracting commonly-held-information which is common to the sentence-constituting-elements in the same category from the sentence-constituting-elements; looking up common expression information which is common to plural pieces of the commonly-held-information in a thesaurus in which the commonly-held-information and the common expression information are connected by a hierarchical tree; and composing a summary based on the commonly-held-information and the common expression information.

18 Claims, 8 Drawing Sheets

FIG.2

··· COMPANY A UPWARDLY CORRECTED ANNUAL SALES PROSPECT. ···

···

COMPANY A ESTABLISHED A SOFTWARE COMPANY IN TAIWAN IN SEPTEMBER, '95. ···

··· COMPANY B UPWARDLY CORRECTED ANNUAL SALES PROSPECT. ···

··· COMPANY B ESTABLISHED A SOFTWARE VENTURE COMPANY IN HONG KONG IN APRIL, '95. ···

··· COMPANY C ESTABLISHED A COLOR TELEVISION PLANT IN CHINA IN DECEMBER, '95. ···

FIG.3

| SENTENCE NO. | WHEN | WHO | WHERE | WHAT | DONE |
|---|---|---|---|---|---|
| ... | ... | ... | ... | ... | ... |
| No.3 | — | COMPANY A | — | ANNUAL SALES PROSPECT | UPWARDLY CORRECT |
| ... | ... | ... | ... | ... | ... |
| No.7 | SEPTEMBER, '95 | COMPANY A | TAIWAN | SOFTWARE COMPANY | ESTABLISH |
| ... | ... | ... | ... | ... | ... |
| No.16 | — | COMPANY B | — | ANNUAL SALES PROSPECT | UPWARDLY CORRECT |
| ... | ... | ... | ... | ... | ... |
| No.23 | APRIL, '95 | COMPANY B | HONG KONG | SOFTWARE VENTURE COMPANY | ESTABLISH |
| ... | ... | ... | ... | ... | ... |
| No.51 | DECEMBER, '95 | COMPANY C | CHINA | COLOR TELEVISION PLANT | ESTABLISH |
| ... | ... | ... | ... | ... | ... |

F I G. 5

| SENTENCE NO. | WHEN | WHO | WHERE | WHAT | DONE |
|---|---|---|---|---|---|
| No. 7 & No. 23 | '95 | TWO COMMUNICATION & COMPUTER COMPANIES | EASTERN ASIA | SOFTWARE COMPANIES | ESTABLISH |
| No. 7 & No. 23 & No. 51 | '95 | THREE ELECTRONICS COMPANIES | EASTERN ASIA | SOFTWARE COMPANIES AND A COLOR TELEVISION PLANT | ESTABLISH |

| SENTENCE NO. | WHEN | WHO | WHERE | WHAT | DONE |
|---|---|---|---|---|---|
| No. 7 & No. 23 | '95 | TWO COMMUNICATION & COMPUTER COMPANIES WHICH UPWARDLY CORRECT ANNUAL SALES PROSPECT | EASTERN ASIA | SOFTWARE COMPANIES | ESTABLISH |

··· COMPANY A ESTABLISHED A SEMICONDUCTOR PLANT IN KOREA IN JANUARY, '93. ···

··· COMPANY A ESTABLISHED A SOFTWARE COMPANY IN TAIWAN IN SEPTEMBER, '95. ···

··· COMPANY B ESTABLISHED A PERSONAL COMPUTER PLANT IN TAIWAN IN JUNE, '94. ···

METHOD, APPARATUS, AND COMPUTER PROGRAM PRODUCT FOR GENERATING A SUMMARY OF A DOCUMENT BASED ON COMMON EXPRESSIONS APPEARING IN THE DOCUMENT

BACKGROUND OF THE INVENTION

1. Field of the Invention

The present invention relates to a method, an apparatus, and a computer program product for making a summary of a document on the basis of commonly owned information and relation between ideas found in the sentences in the document.

2. Description of the Prior Art

In a computer-aided automatic summarizing system, important sentences are selected from the sentences in a document according to an important-sentence selecting rule, and then, a summary is made from the important sentences according to a summarizing rule.

Examples of summarizing techniques using an important-sentence selecting rule are disclosed in Japanese Patent Laid-Open Publication Nos. 2-93866 and 2-112069. In these examples, keywords are selected among words in a document based on the frequency distribution of occurrence of the same word, database of keywords, and user's decision, and then, important sentences containing the keywords are selected. Japanese Patent Laid-Open Publication No. 2-215049 discloses a technique to select important parts from a document by analyzing context vectors. Moreover, Japanese Patent Laid-Open Publication No. 3-191475 discloses a technique to select important sentences from a document by applying a rule reflecting the feature of each paragraph to sentences therein.

The technique of automatically making a summary of a document by gathering sentences containing keywords inevitably requires the use of database of keywords in making a decision as to whether or not each sentence contains keywords, and therefore, the resultant summary is likely to be affected by the contents of the database, and the contents of the summary may be biased or lack flexibility.

The technique of automatically making a summary of a document on the basis of the structure of the document such as the context thereof or the feature of the paragraphs therein is suitable for selecting the structure of a long document and catching the transition of the subject of a long document, but is not suitable for creating a compact summary of high-accuracy.

The technique of making a summary from a collection of important sentences in a document requires an effective method for collecting information common to the important sentences and generating a compact expression reflecting the common information. However, such method has not been proposed as yet.

SUMMARY OF THE INVENTION

An object of the present invention is to provide a method, an apparatus, and a computer program product for generating from a document an accurate and compact summary on which the point of view of a user is reflected.

According to the present invention, there is provided method of summarizing a document which comprises the steps of: extracting sentence-constituting-elements from the document; tabularizing the sentence-constituting-elements corresponding to categories and sentences in the document; extracting commonly-held-information which is common to the sentence-constituting-elements in the same category from the sentence-constituting-elements; looking up common expression information which is common to plural pieces of the commonly-held-information in a thesaurus in which the commonly-held-information and the common expression information are connected by a hierarchical tree; and composing a summary based on the commonly-held-information and the common expression information.

Sentence-constituting-elements which come under predetermined categories are extracted from a document. The predetermined categories includes "When", "Where", "Who", "What", "Why", "How" (5W1H) and "Done". The extracted sentence-constituting-elements are categorized based on the categories. The categorized sentence-constituting-elements are referred to as categorized information. The categorized information which is subjected to generation of the framework of a sentence in a summary is referred to as commonly-held-information. The common expression information which is common to commonly-held-information is extracted consulting a thesaurus. The categorized information which is subjected to generation of the qualifying part of a sentence in the summary is referred to as commonly-occurring-information. A sentence in the summary is generated from pieces of commonly-held-information, pieces of common expression information and optionally from pieces of commonly-occurring-information.

These and other objects, features and advantages of the present invention will become more apparent in light of the following detailed description of the best mode embodiments thereof, as illustrated in the accompanying drawings.

DESCRIPTION OF PREFERRED EMBODIMENTS

Figure 1:
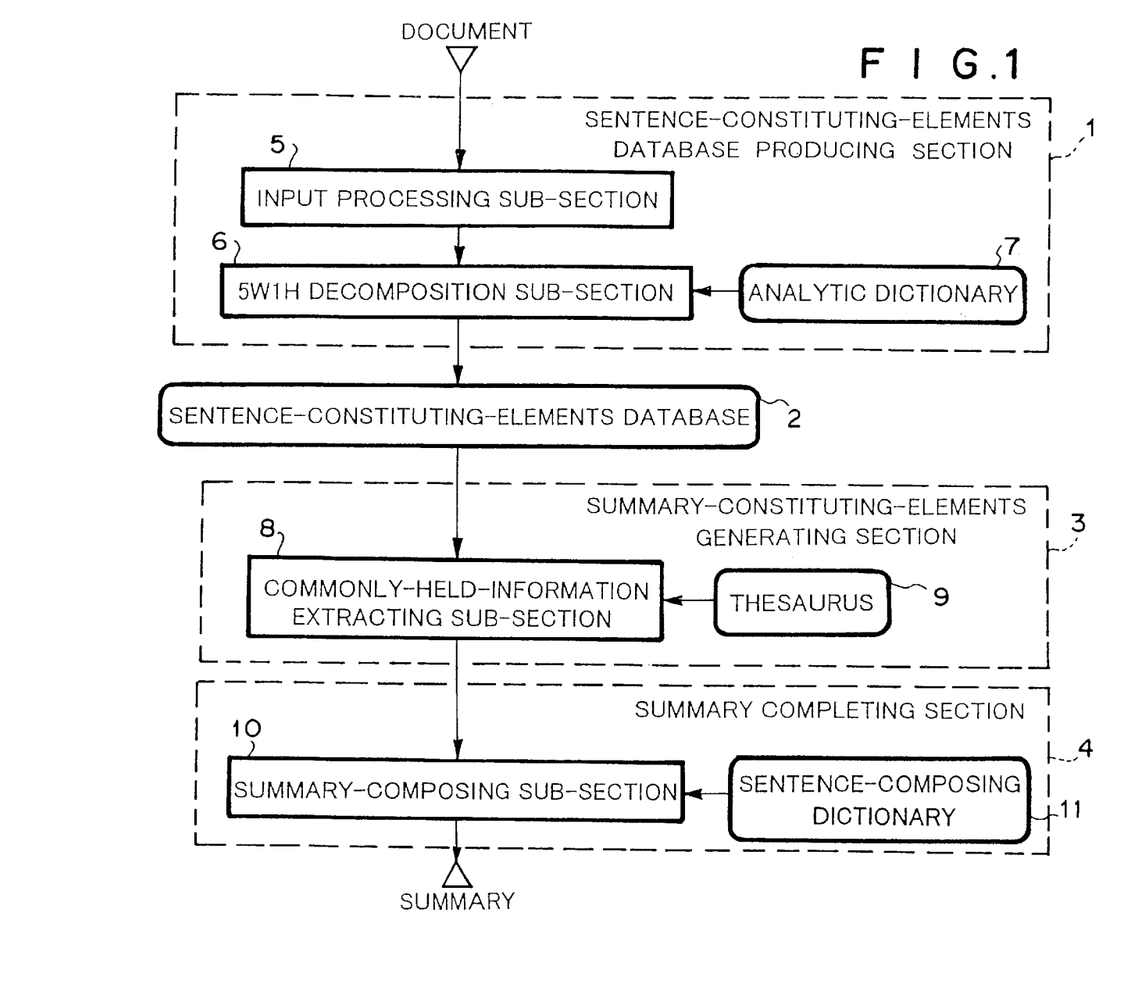
FIG. 1 is a block diagram showing the basic structure of a summarizing apparatus according to a first embodiment of the present invention.

Referring to FIG. 1, a summarizing apparatus according to a first embodiment of the present invention comprises sentence-constituting-elements database producing section 1 which extracts sentence-constituting-elements corresponding to each of categories from a document and output the sentence-constituting-elements accompanied by the corresponding categories; sentence-constituting-elements database 2 which stores the sentence-constituting-elements dividedly according to the categories; summary-constituting-elements generating section 3 which extracts pieces of commonly-held-information corresponding to the categories from the sentence-constituting-elements and extracts pieces of common expression information which are common to pieces of commonly-held-information; and summary completing section 4 which generates a summary based on pieces of commonly-held-information and pieces of common expression information. The categories include "When", "Where", "Who", "What", "Why", "How" (5W1H) and "Done".

The sentence-constituting-elements database producing section 1 comprises input processing sub-section 5 which executes preprocessing such as morphology analysis to generate preprocessed information, analytic dictionary 7 which stores data used for analyzing the preprocessed information, and 5W1H decomposing sub-section 6 which analyzes the preprocessed information sentence by sentence consulting analytic dictionary 7 to generate sentence-constituting-elements corresponding to categories.

Sentence-constituting-elements database 2 stores sentence-constituting-elements. Fields of sentence-constituting-elements database 2 are categories and each record of sentence-constituting-elements database 2 corresponds to a sentence in the original document.

Summary-constituting elements generating section 3 comprises commonly-held-information extracting sub-section 8 which extracts and outputs commonly-held-information corresponding to each of attributes from sentence-constituting-elements and thesaurus 9 in which hierarchical trees of common expression information and commonly-held-information are stored. In addition to extracting commonly-held-information, commonly-held-information extracting sub-section 8 finds common expression information consulting thesaurus 9 and outputs the commonly-held-information and the common expression information to summary completing section 4.

Summary completing section 4 comprises sentence-composing dictionary 11 in which data used for composing a sentence are stored and sentence-composing sub-section 10 which composes a summary from the commonly-held-information and common expression information consulting sentence-composing dictionary 11.

Next, the operation of the summarizing apparatus according to the first embodiment will be explained by example.

Figure 2:
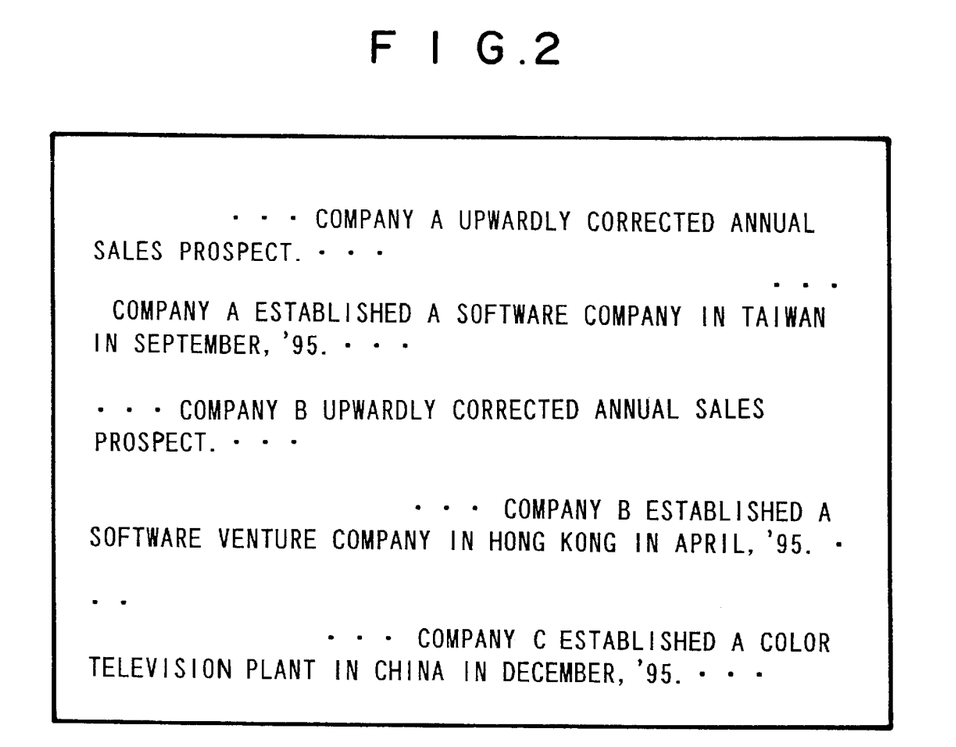
FIG. 2 shows one example of a document supplied to input processing sub-section 5 of sentence-constituting-elements database producing section 1 in FIG. 1.
Figure 3:
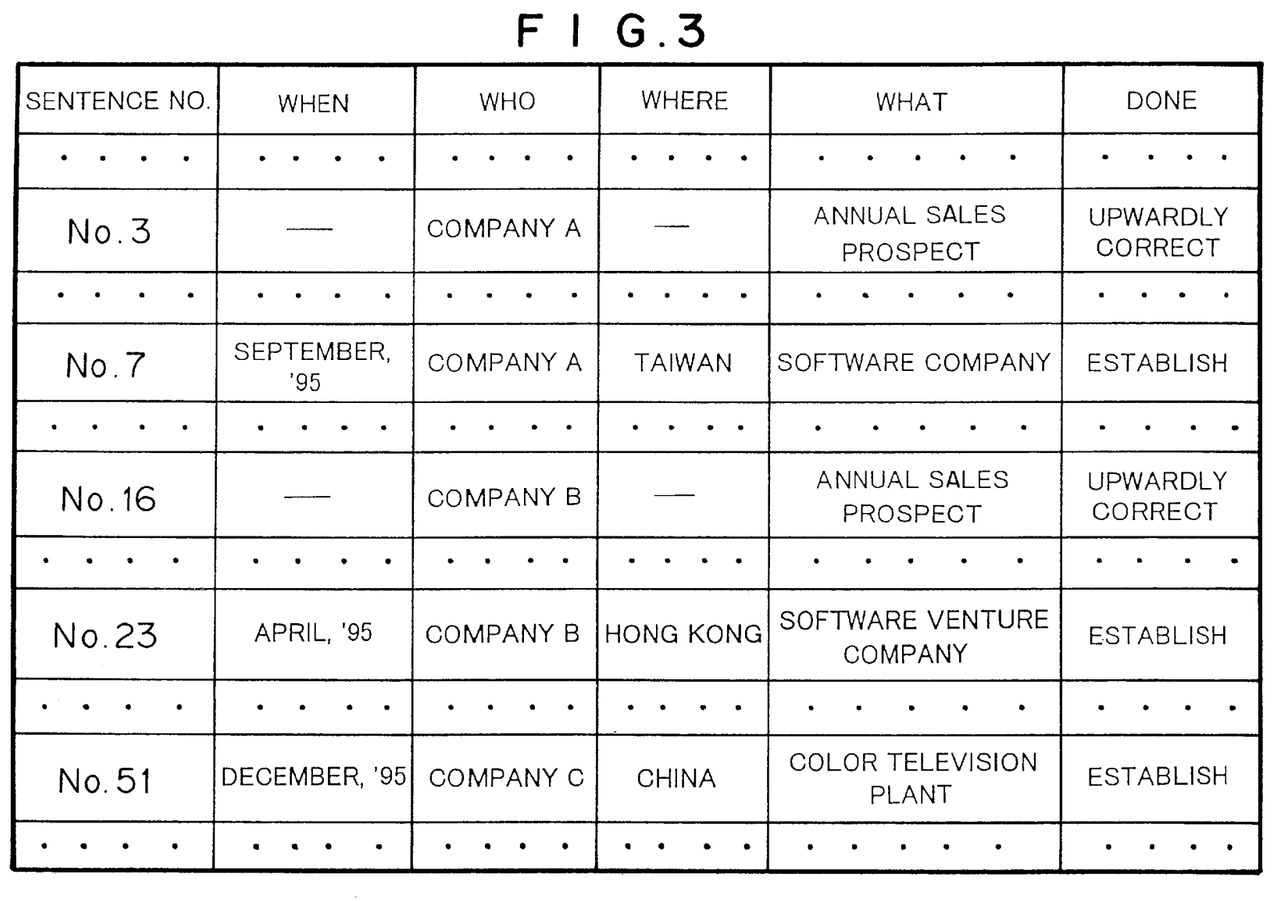
FIG. 3 shows, in the form of table, one example of sentence-constituting-elements stored in sentence-constituting-elements database 2 in FIG. 1.
Figure 4:
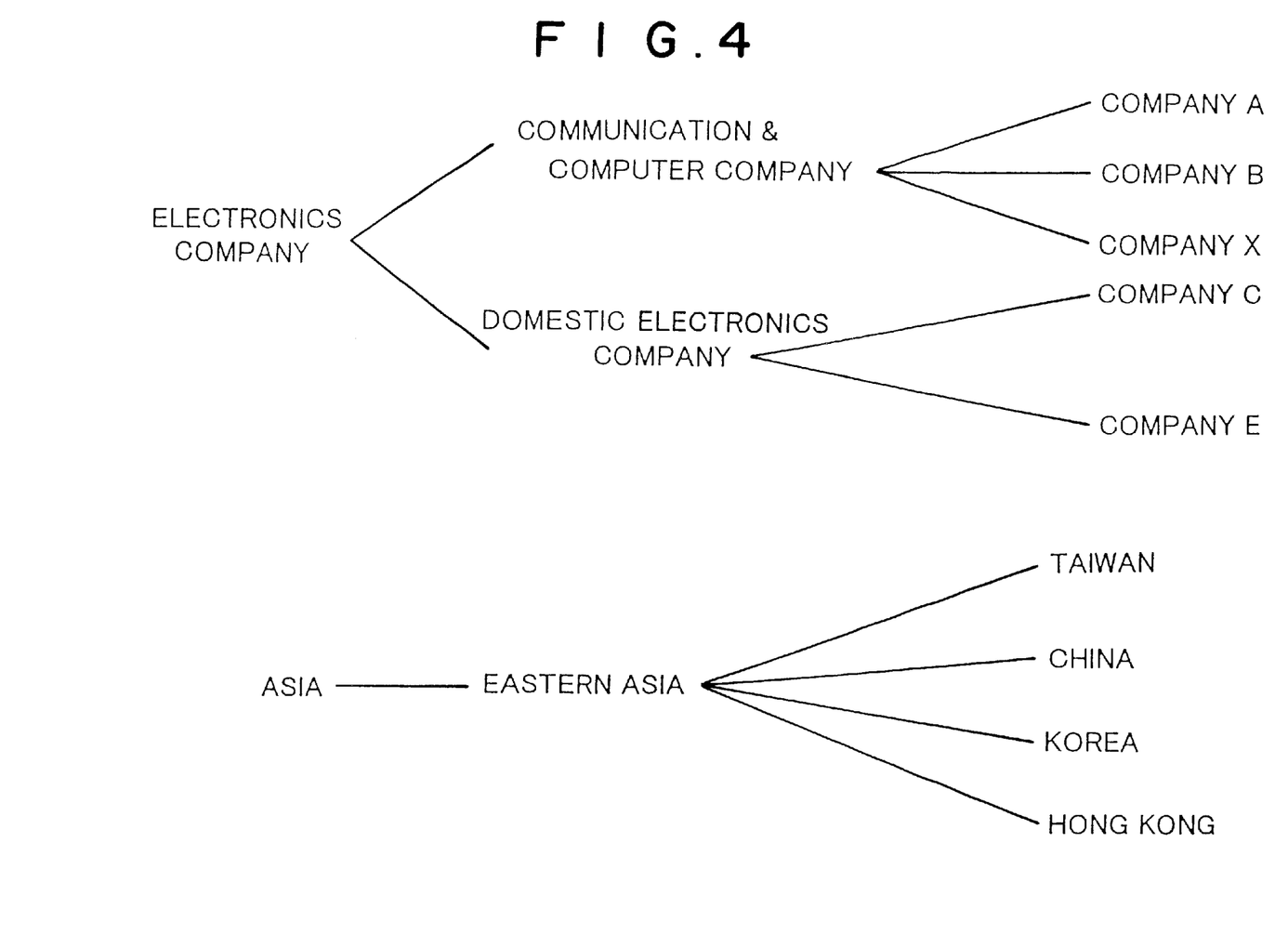
FIG. 4 shows examples of the contents of thesaurus 9 contained in summary-constituting-elements generating 3 section in FIG. 1.

The document as shown in FIG. 2 is supplied to input processing sub-section 5 of sentence-constituting-elements database producing section 1. The document includes three sentences, which are: "Company A established a software company in Taiwan in September, '95."; "Company B established a software venture company in Hong Kong in April, '95."; and "Company C established a color television plant in China in December, '95." 5W1H decomposition sub-section 6 extracts sentence-constituting-elements for every sentence in the documents and all the categories consulting analytic dictionary 7 and supplies the sentence-constituting-elements to sentence-constituting-elements database 2 in which a group of the sentence-constituting-elements in one sentence is treated as one record and each member of the group is recorded in a corresponding field representing one of categories as shown in FIG. 3. In summary-constituting-elements generating section 3, commonly-held-information extracting sub-section 8 extracts "'95" as commonly-held-information for category "when" from sentences 7, 23 and 51, and "establish" as commonly-held-information for category "done" from sentences 7, 23 and 51. In addition, consulting thesaurus 9 as shown in FIG. 4, commonly-held-information extracting sub-section 8 extracts "three electronics companies" as common expression information for category "who" from sentences 7, 23, and 51, "two communication & computer companies" as common expression information for category "who" from sentences 7 and 23, "Eastern Asia" for category "where" from sentences 7, 23, and 51, "software companies and a color television plant" for category "what" from sentences 7, 23, and 51, "software companies" for category "what" from sentences 7 and 23. The extracted commonly-held-information and common expression information are tabled in FIG. 5.

Figure 5:
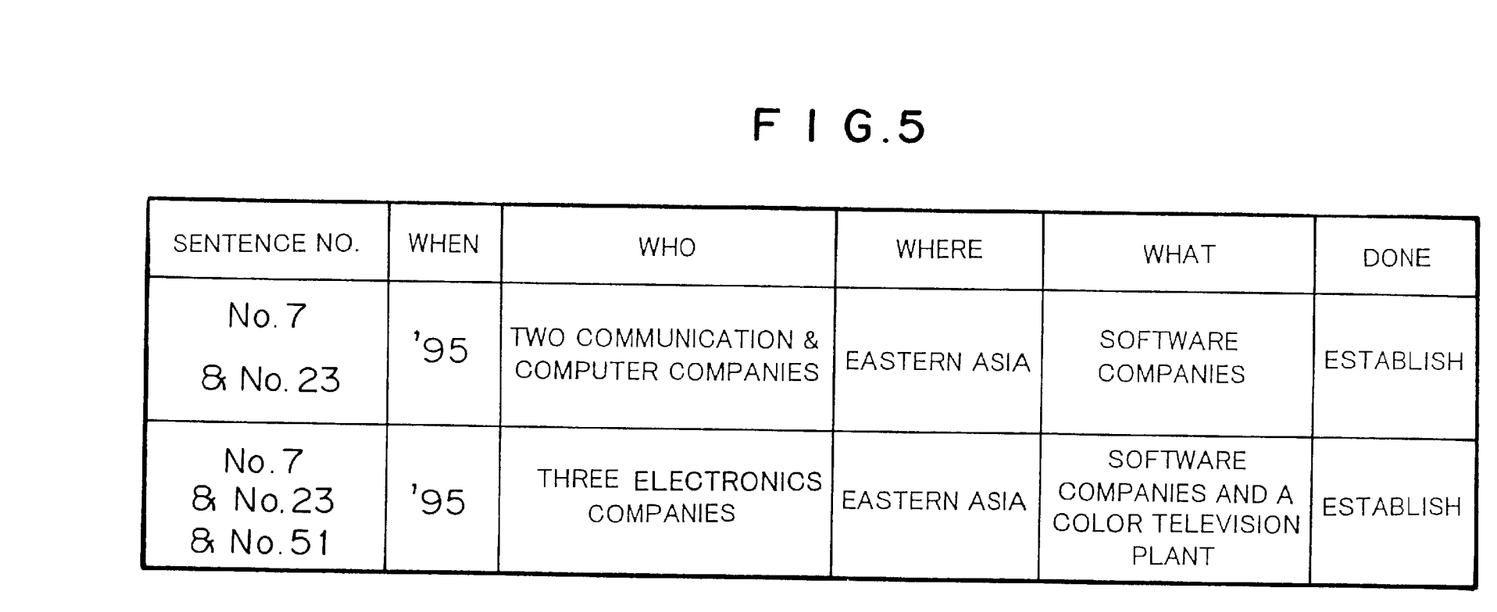
FIG. 5 shows, in the form of table, one example of commonly-held-information and common expression information which is extracted in commonly-held-information extracting sub-section 7 in FIG. 1.

Summary completing section 4 generates a summary from the commonly-held-information and the common expression information as follows:

"Two communication & computer companies established software companies in Eastern Asia in '95." and "Three electronics companies established software companies and color television plant in Eastern Asia in '95.".

EMBODIMENT 2

Figure 6:
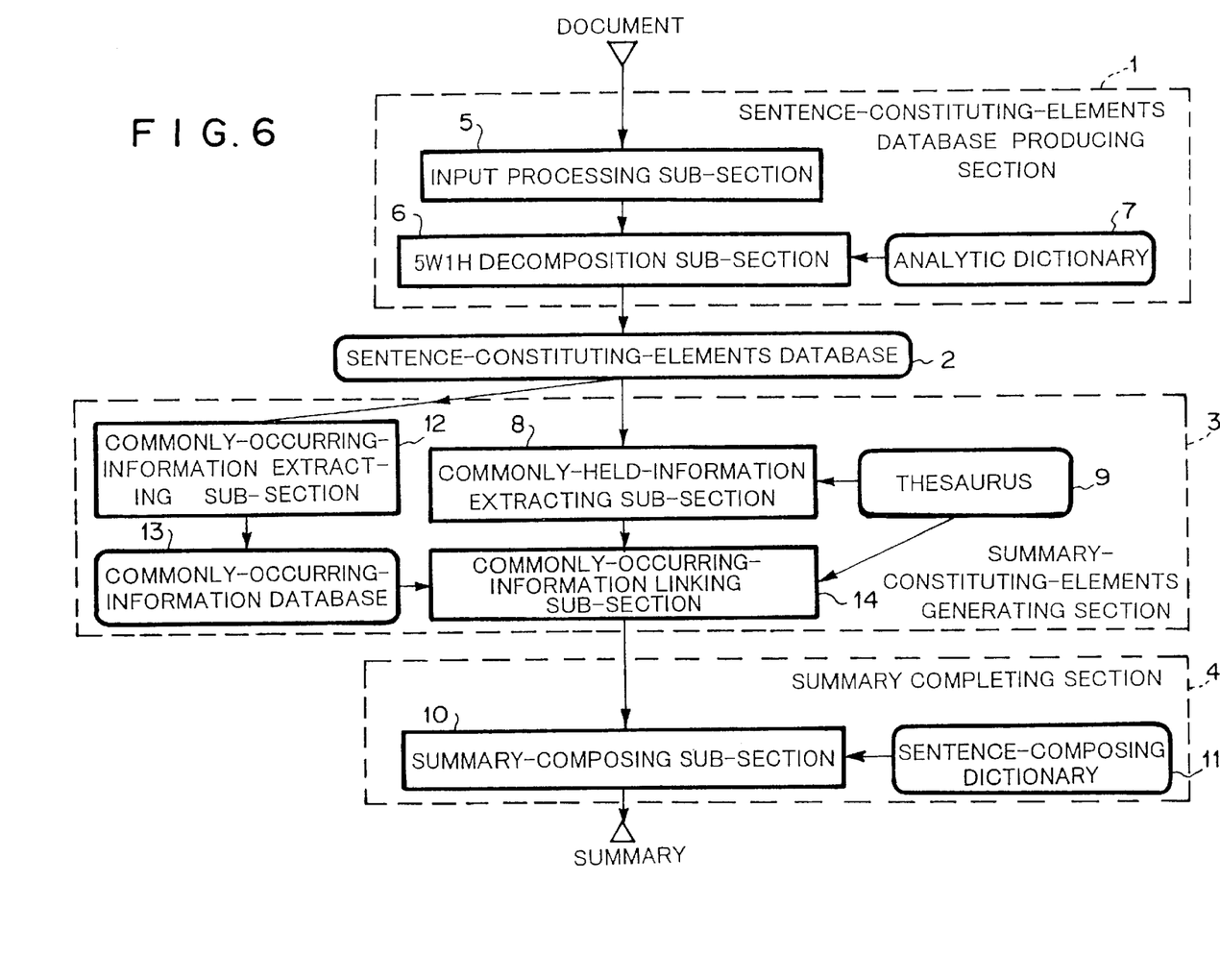
FIG. 6 is a block diagram showing the basic structure of a summarizing apparatus according to a second embodiment of the present invention.

FIG. 6 shows the basic structure of a summarizing apparatus according to a second embodiment of the present invention.

In addition to the steps of the first embodiment, in this embodiment, commonly-occurring-information which commonly occurs in plural records is extracted, and is linked to commonly-held-information or common expression information, thereby summary-constituting-elements can be extended.

As shown in FIG. 6, in addition to commonly-held-information extracting sub-section 8 and thesaurus 9, summary-constituting-elements generating section 3 comprises commonly-occurring-information extracting sub-section 12 which extracts commonly-occurring-information which commonly occurs in plural records from sentence-constituting-elements database 2, commonly-occurring-information database 13 which stores the commonly-occurring-information, and commonly-occurring-information linking sub-section 14 which links the commonly-occurring-information to commonly-held-information or common expression information.

Assuming that the document as shown in FIG. 2 is supplied to input processing sub-section 5 similarly to the first embodiment, sentence-constituting-elements database 2 stores the sentence-constituting-elements as shown in FIG. 3 and commonly-held-information extracting sub-section 8 extracts commonly-held-information and common expression information as shown in FIG. 5. The operation described so far is similar to that of the summarizing apparatus of the first embodiment.

Figure 7:
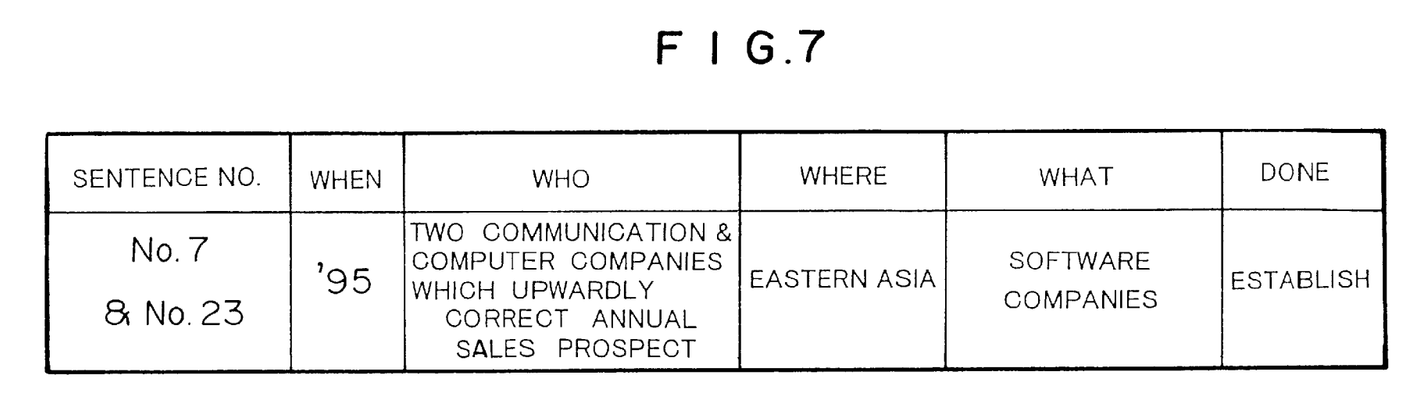
FIG. 7 shows one example of a set consisting of common expression information, common expression information linked to commonly-occurring-information, and commonly-held-information which is generated by from commonly-occurring-information linking sub-section 14 in FIG. 6.

Commonly-occurring-information extracting sub-section 12 extracts commonly-occurring-information which commonly occurs in plural records. But exact correspondency among records is not required. Only partial correspondency among records is required. For example, sentence-constituting-elements common to several "who"s are extracted as commonly-occurring-information. In this case, commonly-occurring-information extracting subsection 12 extracts "annual sales prospect" and "upwardly correct" as commonly-occurring-information which are common to company A and B. Subsequently, commonly-occurring-information extracting sub-section 12 stores the commonly-occurring-information to commonly-occurring-information database 13. Commonly-occurring-information linking sub-section 14 links commonly-occurring-information stored in commonly-occurring-information database 13 to commonly-held-information or common expression information consulting thesaurus 9. The reason why commonly-occurring-information linking subsection 14 consult thesaurus 9 is "who"s for the same commonly-occurring-information may be grouped in thesaurus 14. As a result, commonly-occurring-information linking sub-section 14 outputs common expression information linked to commonly-occurring-information as shown in FIG. 7. In general, commonly-occurring-information linking sub-section 14 may outputs commonly-held-information linked to commonly-occurring-information.

Summary completing section 4 generates a summary from commonly-held-information, common expression information, and common expression information linked commonly-occurring-information. The summary in this example becomes "Two communication & computer companies which upwardly corrected annual sales prospect established software companies in Eastern Asia in '95.".

EMBODIMENT 3

A summarizing apparatus according to a third embodiment of the present invention comprises a plurality of thesaurus associated with commonly-held-information extracting sub-section 8. These thesauri are provided for variety of fields of knowledge to generate various summaries.

Figure 8:
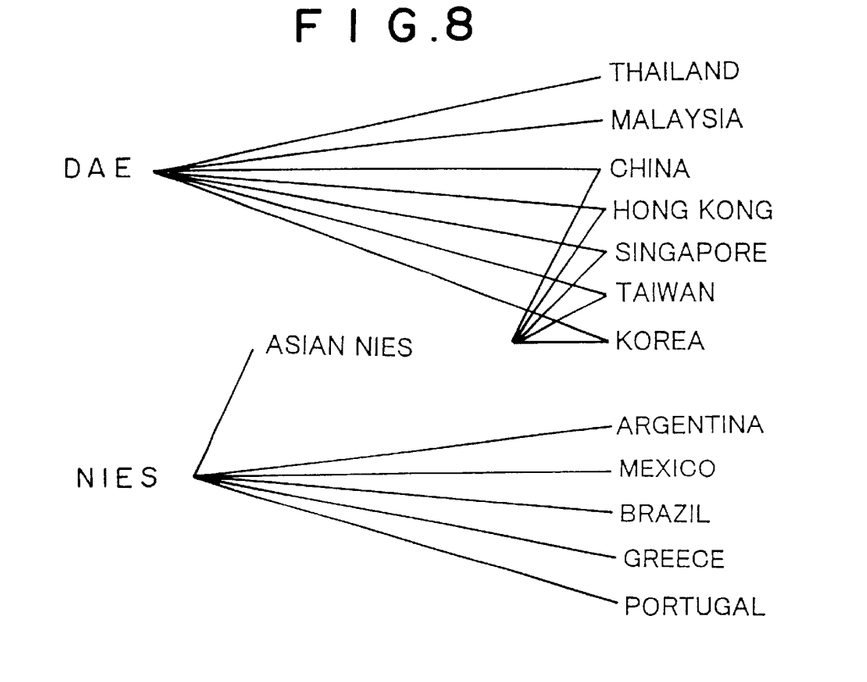
FIG. 8 shows examples of the contents of thesaurus 9 according to a third embodiment.

Assuming that the document as shown in FIG. 2 is supplied to input processing sub-section 5 similarly to the first and second embodiments, sentence-constituting-elements database 2 stores sentence-constituting-elements as shown in FIG. 3. In addition to the thesaurus covering the geographical field as shown in FIG. 4, a thesaurus covering the global-financial field as shown in FIG. 8 is provided. The latter thesaurus is use in this embodiment.

Commonly-held-information extracting sub-section extract "Asian NIES" as common expression information for category "where" from sentences 7, 23, and 51 consulting the thesaurus shown in FIG. 8. The resultant summary becomes "Two communication & computer companies established software companies in Asia NIES in '95."

EMBODIMENT 4

In this embodiment, commonly-held-information extracting sub-section 8 extracts commonly-held-information according to the priority of categories made by a user, whereby a summary reflecting information of user's strong interest can be generated with flexibility.

Figure 9:
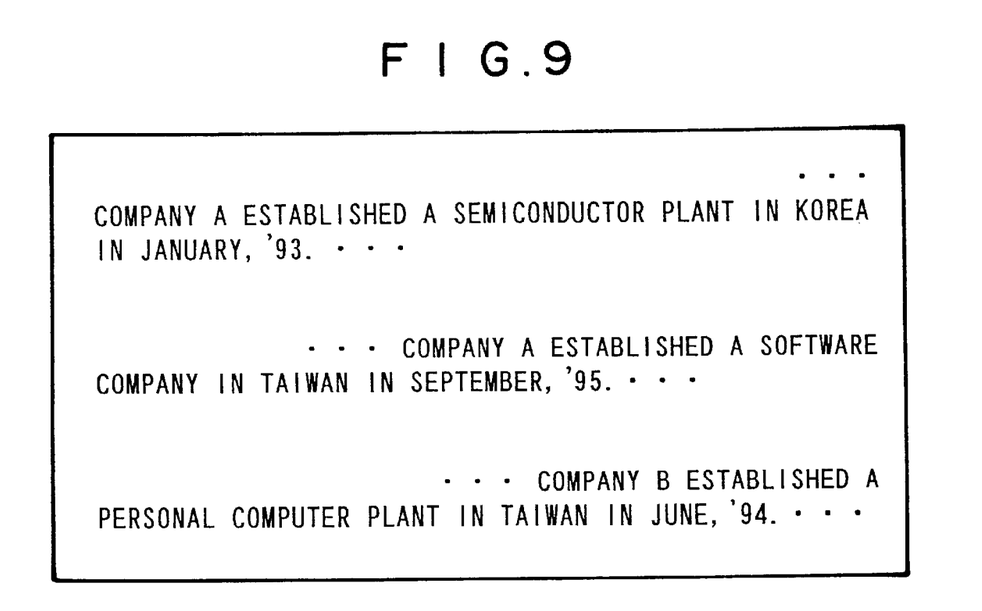
FIG. 9 shows one example of a document supplied to input processing sub-section 5 in a summarizing apparatus according to a fourth embodiment.

Assuming that the document containing "Company A established a semiconductor plant in Korea in January, '93.", "Company A established a software company in Taiwan in September, '95.", and "Company B established a personal computer plant in Taiwan in June, '94." as shown in FIG. 9 is supplied to input processing sub-section 5.

When priority is given to "Who" and "What", the resultant summary becomes "Company A established a semiconductor plant and a software company in Eastern Asia in '93 and '95, respectively.".

When priority is given to "Where" and "Done", the resultant summary becomes "Two communication & computer companies established a personal computer plant and a software company in Taiwan in '94 and '95, respectively.".

Preferably, the present invention is a computer program executing in a computer system which comprises a central processing unit, a main memory, a secondary memory, and a bus connecting the central processing unit, the main memory, and the secondary memory. The computer program is stored in the secondary memory. The computer program resides in the main memory during execution. The computer program includes instructions which causes the central processing unit to perform the functions or methods explained above.

Although the present invention has been shown and explained with respect to the best mode embodiments thereof, it should be understood by those skilled in the art that the foregoing and various other changes, omissions, and additions in the form and detail thereof may be made therein without departing from the spirit and scope of the present invention.

What is claimed is:

1. A method of preparing a document summary which comprises the steps of:
   extracting sentence-constituting-elements from the document;
   classifying said sentence-constituting-elements into categories;
   extracting commonly-held-information which is common to said sentence-constituting-elements in the same;
   looking up common expression information which is common to plural pieces of said commonly-held-information in a thesaurus in which said commonly-held-information and said common expression information are connected by a hierarchical tree; and
   composing the document summary based on said commonly-held-information and said common expression information;
      wherein said categories include "When", "Where", "Who", "What", "Why", "How" and "Done".

2. The method as set forth in claim 1, wherein more than one thesaurus are provided and one of said thesauri is selected corresponding to a user's operation.

3. The method as set forth in claim 1, which further comprises the steps of:
   extracting commonly-occurring-information which is common to several sentences in said document in one or more categories; and
   linking said commonly-occurring-information to said commonly-held-information or said common expression information.

4. The method as set forth in claim 1, wherein priority is given to a part of said categories corresponding to a user's operation.

5. The method as set forth in claim 1, wherein each sentence of the document summary is composed by selectively combining pieces of said commonly-held-information and said common expression information.

6. An apparatus for generating a document summary which comprises:
   means for extracting sentence-constituting-elements from the document;
   means for classifying said sentence-constituting-elements into categories;
   means for extracting commonly-held-information which is common to said sentence-constituting-elements in the same;

a thesaurus in which said commonly-held-information and common expression information are connected by a hierarchical tree;

means for looking up said common expression information which is common to plural pieces of said commonly-held-information in said thesaurus; and means for composing the document summary based on said commonly-held-information and said common expression information;

wherein said categories include "When", "Where", "Who", "What", "Why", "How" and "Done".

7. The apparatus as set forth in claim 6, wherein more than one thesaurus are provided and the apparatus further comprises means for selecting one of said thesauri corresponding to a user's operation.

8. The apparatus as set forth in claim 6, which further comprises means for giving priority to a part of said categories corresponding to a user's operation.

9. The apparatus as set forth in claim 6, wherein said means for composing produces each sentence of the document summary and includes means for selectively combining pieces of said commonly-held-information and said common expression information to produce each sentence.

10. The apparatus set forth in claim 6, which further comprises:

means for extracting commonly-occurring-information which is common to several sentences in said document in one or more categories; and means for linking said commonly-occurring information to said commonly-held-information or said common expression information.

11. A method for generating a summary sentence from a document, said method comprising the steps of:

extracting sentence-constituting-elements from each sentence in the document;

classifying said sentence-constituting-elements into categories for each sentence in the document;

extracting a common word which is common to the sentence-constituting-elements extracted from all of or a part of the sentences in the document for each category;

looking up a generic word which is common to the sentence-constituting-elements extracted from all of or a part of the sentences in the document from a thesaurus in which generic words and specific words are connected in a hierarchical tree for each category on behalf of the extracting step if possible; and composing the summary sentence comprising the extracted common words and the looked-up generic words, wherein said categories include "When", "Where", "Who", "What", "Why", "How" and "Done".

12. An apparatus for generating a summary sentence from a document, said apparatus comprising:

means for extracting sentence-constituting-elements from each sentence in the document;

means for classifying said sentence-constituting-elements into categories for each sentence in the document;

means for extracting a common word which is common to the sentence-constituting-elements extracted from all of or a part of the sentences in the document for each category;

means for looking up a generic word which is common to the sentence-constituting-elements extracted from all of or a part of the sentences in the document from a thesaurus in which generic words and specific words are connected in a hierarchical tree for each category on behalf of the extracting step if possible; and means for composing the summary sentence comprising the extracted common words and the looked-up generic words;

wherein said categories include "When", "Where", "Who", "What", "Why", "How" and "Done".

13. A computer program product comprising a computer useable medium having a computer program logic stored therein, said computer program logic causing a computer to execute the steps of:

extracting sentence-constituting-elements from each sentence in the document;

classifying said sentence-constituting-elements into categories for each sentence in the document;

extracting a common word which is common to the sentence-constituting-elements extracted from all of or a part of the sentences in the document for each category;

looking up a generic word which is common to the sentence-constituting-elements extracted from all of or a part of the sentences in the document from a thesaurus in which generic words and specific words are connected in a hierarchical tree for each category on behalf of the extracting step if possible; and composing the summary sentence comprising the extracted common words and the looked-up generic words;

wherein said categories include "When", "Where", "Who", "What", "Why", "How" and "Done".

14. A computer program product comprising a computer useable medium having structured data and computer program logic stored therein, said structured data comprising:

a thesaurus in which commonly-held-information and common expression information are connected by a hierarchical tree; and said computer program logic comprising:

means for extracting sentence-constituting-elements from the document;

means for classifying said sentence-constituting-elements into categories;

means for extracting commonly-held-information which is common to said sentence-constituting-elements in the same category;

means for looking up said common expression information which is common to plural pieces of said commonly-held-information in said thesaurus; and means for composing the document summary based on said commonly-held-information and said common expression information;

wherein said categories include "When", "Where", "Who", "What", "Why", "How" and "Done".

15. The method as set forth in claim 14, wherein more than one thesaurus are provided and said computer program logic further comprises means for selecting one of said thesauri corresponding to a user's operation.

16. The computer program product as set forth in claim 14, wherein said computer program logic further comprises:

means for extracting commonly-occurring-information which is common to several sentences in said document in one or more categories; and means for linking said commonly-occurring-information to said commonly-held-information or said common expression information.

17. The computer program product as set forth in claim 14, wherein said computer program logic further comprises means for giving priority to a part of said categories corresponding to a user's operation.

18. The computer program product as set forth in claim 14, wherein said means for composing produces each sentence of the document summary and includes means for selectively combining pieces of said commonly-held-information and said common expression information to produce each sentence.

* * * * *